(12) United States Patent
Thompson et al.

(10) Patent No.: US 7,371,235 B2
(45) Date of Patent: *May 13, 2008

(54) ABLATION SYSTEMS INCLUDING INSULATED ENERGY TRANSMITTING ELEMENTS

(75) Inventors: Russell B. Thompson, Los Altos, CA (US); Robert R. Burnside, Mountain View, CA (US); David K. Swanson, Campbell, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 88 days.

This patent is subject to a terminal disclaimer.

(21) Appl. No.: 11/199,001

(22) Filed: Aug. 8, 2005

(65) Prior Publication Data

US 2005/0288667 A1    Dec. 29, 2005

Related U.S. Application Data

(63) Continuation of application No. 10/139,091, filed on May 3, 2002, now Pat. No. 6,932,813.

(51) Int. Cl.
*A61B 18/14* (2006.01)

(52) U.S. Cl. ......................................... 606/41
(58) Field of Classification Search ................... 606/41
See application file for complete search history.

(56) References Cited

U.S. PATENT DOCUMENTS

| | | | |
|---|---|---|---|
| 4,976,711 A | 12/1990 | Parins et al. |
| 5,080,660 A | 1/1992 | Buelna |
| 5,500,012 A | 3/1996 | Brucker et al. |
| 5,683,366 A | 11/1997 | Eggers et al. |
| 5,785,706 A | 7/1998 | Bednarek |
| 5,846,238 A | 12/1998 | Jackson et al. |
| 5,860,974 A | 1/1999 | Abele |
| 5,919,188 A | 7/1999 | Shearon et al. |
| 5,961,513 A | 10/1999 | Swanson et al. |
| 6,001,093 A | 12/1999 | Swanson et al. |
| 6,004,269 A | 12/1999 | Crowley et al. |
| 6,010,500 A | 1/2000 | Sherman et al. |
| 6,064,902 A | 5/2000 | Haissaguerre et al. |
| 6,168,593 B1 | 1/2001 | Sharkey et al. |
| 6,216,027 B1 | 4/2001 | Willis et al. |

(Continued)

*Primary Examiner*—Lee S. Cohen
(74) *Attorney, Agent, or Firm*—Vista IP Law Group LLP

(57) ABSTRACT

Ablation systems comprise a support body, an energy transmitting element supported by the support body and an insulating member covering a portion of the support body and energy transmitting member. Ablation energy is transmitted from an uncovered, exposed portion of the energy transmitting element. The insulating member may be a distal portion of an introducer sheath. An open segment may be provided in the distal portion to expose a portion of the energy transmitting element. When used in cardiac ablation therapy, for example, the insulating member decreases the amount of ablation energy dissipated in the blood circulating through the heart and thermally insulates the energy transmitting member and the tissue at the ablation site, enabling better control of the ablation process. An inflatable balloon or an expandable web may be provided coupled to the distal portion of the sheath behind the open segment to provide further insulation of the energy transmitting element and of the tissue around the ablation site. In another embodiment, ablation catheters incorporate an insulating member such as the inflatable balloon, expandable web or a cover. Methods of ablating tissue are also disclosed.

15 Claims, 9 Drawing Sheets

U.S. PATENT DOCUMENTS

| | | |
|---|---|---|
| 6,241,724 B1 | 6/2001 | Fleischman et al. |
| 6,264,654 B1 | 7/2001 | Swartz et al. |
| 6,325,797 B1 | 12/2001 | Stewart et al. |
| 6,932,813 B2 * | 8/2005 | Thompson et al. ............ 606/41 |
| 2001/0051803 A1 | 12/2001 | Desai et al. |
| 2002/0087151 A1 * | 7/2002 | Mody et al. .................. 606/41 |
| 2003/0050631 A1 | 3/2003 | Mody et al. |

* cited by examiner

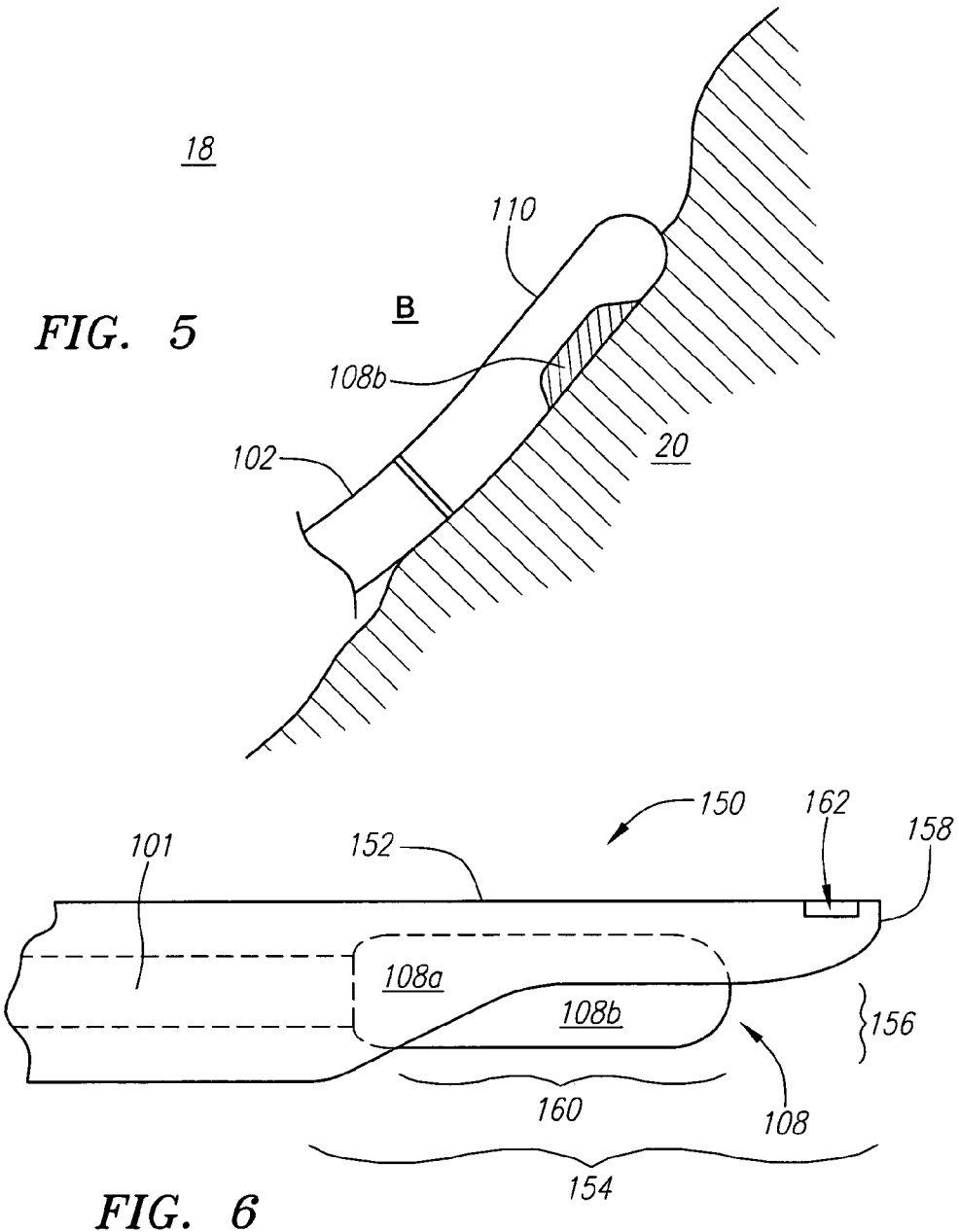
FIG. 5
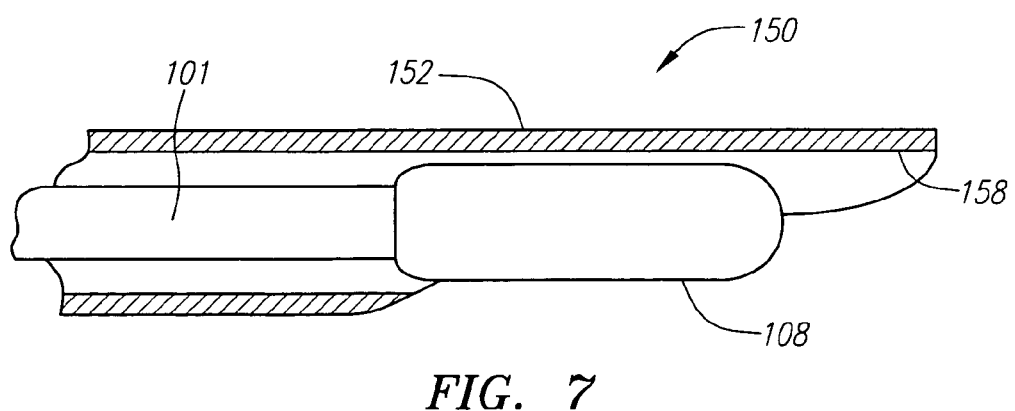
FIG. 6
FIG. 7

ABLATION SYSTEMS INCLUDING INSULATED ENERGY TRANSMITTING ELEMENTS

RELATED APPLICATION DATA

This application is a continuation of U.S. patent application Ser. No. 10/139,091, filed May 3, 2002, now U.S. Pat. No. 6,932,813.

FIELD OF THE INVENTION

Ablation systems for creating lesions in the interior regions of the human body, and more particularly, ablation systems including insulated energy transmitting elements.

BACKGROUND OF THE INVENTION

Physicians frequently use invasive medical devices, such as hand-held probes and catheters, in medical procedures to gain access to interior regions of the body. One type of procedure that has been becoming more widespread is tissue ablation. One example of a tissue ablation procedure is electrophysiology therapy, used to treat cardiac rhythm disturbances (arrhythmia).

In electrophysiology therapy, energy, such as radiofrequency (RF) energy, is used to ablate heart tissue to form a lesion that will block the propagation of aberrant electrical signals. To deliver the RF energy, energy transmitting elements, such as electrodes, are provided at the distal end of an ablation catheter. To access the cardiac tissue, a catheter, referred to as an introducer sheath, is percutaneously inserted into and advanced to the site of interest through a blood vessel, for example, such as the femoral artery. When the distal end of the introducer sheath is proximate the site of interest, the ablation catheter is inserted into the proximal end of the introducer sheath and advanced through the sheath. The distal end of the introducer sheath is open to allow the distal end of the ablation catheter, including the energy transmitting elements, to exit the sheath, and contact tissue at the site of interest. FIG. 1 is a view of a distal end of a typical ablation catheter 10 including an energy transmitting element 12 extending through a distal end 14 of an introducer sheath 16 and bearing against cardiac tissue 18 at an ablation site in a chamber of the heart 20. As shown, the distal end 14 of the introducer sheath 16 is typically straight. The energy transmitting element 12 may be one or more electrodes of tantalum, gold or platinum, for example, electrically connected to a radio frequency power source (not shown). Ablation catheters are described in U.S. Pat. No. 6,241,724 B1, U.S. Pat. No. 6,216,027 B1, and U.S. Pat. No. 6,004,269, for example, which are assigned to the assignee of the present invention and are incorporated by reference herein.

As shown in FIG. 1, only a portion of the circumferential surface of the electrode 12 is in contact with the tissue 20. The remainder of the electrode 12 is in contact with blood "B" circulating through the heart 20. Since the blood is conductive, much of the RF energy emitted by the electrode (as much as 75%) is thermally dissipated in the blood. The amount of RF energy that must be conveyed to electrodes in conventional ablation catheter systems to create even small therapeutic lesions is therefore quite high (up to 50 watts or more).

One or more temperature sensors 22 are typically provided on or in the electrode 12 to detect the temperature of the cardiac tissue being ablated. The temperature is used to control the application of energy to the electrode 12 during the procedure, typically under software control. The circulating blood in the heart acts as a heat sink that dissipates heat from the electrode 12 and from the tissue at the ablation site. Typically, there is a 15°-30° difference between the temperature measured by the sensor 22 and the actual temperature of the tissue. Thermal regulation of the ablation procedure is therefore difficult. Poor thermal regulation can lead to coagulum and popping of the cardiac tissue.

U.S. Pat. No. 6,241,724 B1, mentioned above, discloses an ablation catheter with multiple electrical segments arranged circumferentially around a distal end of the catheter. Each segment is electrically and thermally isolated from an adjacent segment. Independent signal wires are attached to each segment, enabling a physician to independently provide ablation energy to the one or more segments in contact with tissue. Dissipation of energy into the blood pool is decreased and energy efficiency and lesion creation are thereby improved.

Insulated wires have also been used as electrodes in ablation catheters. The insulation is removed from a portion of the circumference of the wire that will contact the tissue. The remainder of the wire, which may be exposed primarily to the circulating blood, is insulated. Less heat and RF energy is dissipated to the blood. Partially insulated coil electrodes are known, as well.

More energy efficient catheter ablation systems with simpler structures would be advantageous.

SUMMARY OF THE INVENTION

In accordance with the invention, the distal portion of an ablation catheter, including a portion of the energy transmitting element, is partially covered with an insulating material, leaving an exposed portion of the energy transmitting element available for transmitting ablation energy. The remainder of the energy transmitting element is electrically and thermally insulated. When used in cardiac ablation, the insulating material electrically and thermally insulates the covered portion of the energy transmitting element from circulating blood, and thermally insulates tissue proximate the ablation site from the circulating blood.

In one embodiment, a system for ablating body tissue is disclosed comprising a support body having a distal end and an energy transmitting element supported by the distal end. An insulating member is provided to cover at least a portion of the support body and a portion of the energy transmitting element. The insulating member may be provided on a distal portion of tubular body, such as an introducer sheath, adapted to receive the distal portion of the support body. The distal portion of the support body and the distal portion of the tubular member may be aligned during use such that the insulting member covers a portion of the energy transmitting element. In a preferred embodiment, the insulating member includes an open segment for exposing a portion of the energy transmitting element to transmit energy to ablate tissue. An inflatable balloon or expandable web may also be provided on the introducer sheath, behind the open segment, to provide further electrical and thermal insulation of the energy transmitting element and the tissue of the ablation site.

In another embodiment of the invention, an ablation device is disclosed comprising a support body, an energy transmitting element supported by the support body and an insulating member coupled to a distal portion of the support body to cover a portion of the distal portion and the energy transmitting element. The support body may be a catheter.

Other embodiments of the invention include introducer sheaths and ablation methods.

BRIEF DESCRIPTION OF THE DRAWINGS

The present invention is illustrated by way of example, and not by way of limitation, in the figures of the accompanying drawings, in which like reference numerals refer to similar elements, and in which:

FIG. 5 shows the distal end of the introducer sheath of FIG. 3a, bearing against and partially embedded in cardiac tissue;

FIG. 6 is a side view of another embodiment of an introducer sheath in accordance with the invention, wherein an open segment includes a portion of the distal end of the introducer sheath;

FIG. 7 is a side view of the distal portion of FIG. 6, with a front half of the distal portion of the sheath removed;

DESCRIPTION OF THE PREFERRED EMBODIMENTS

Figure 2:
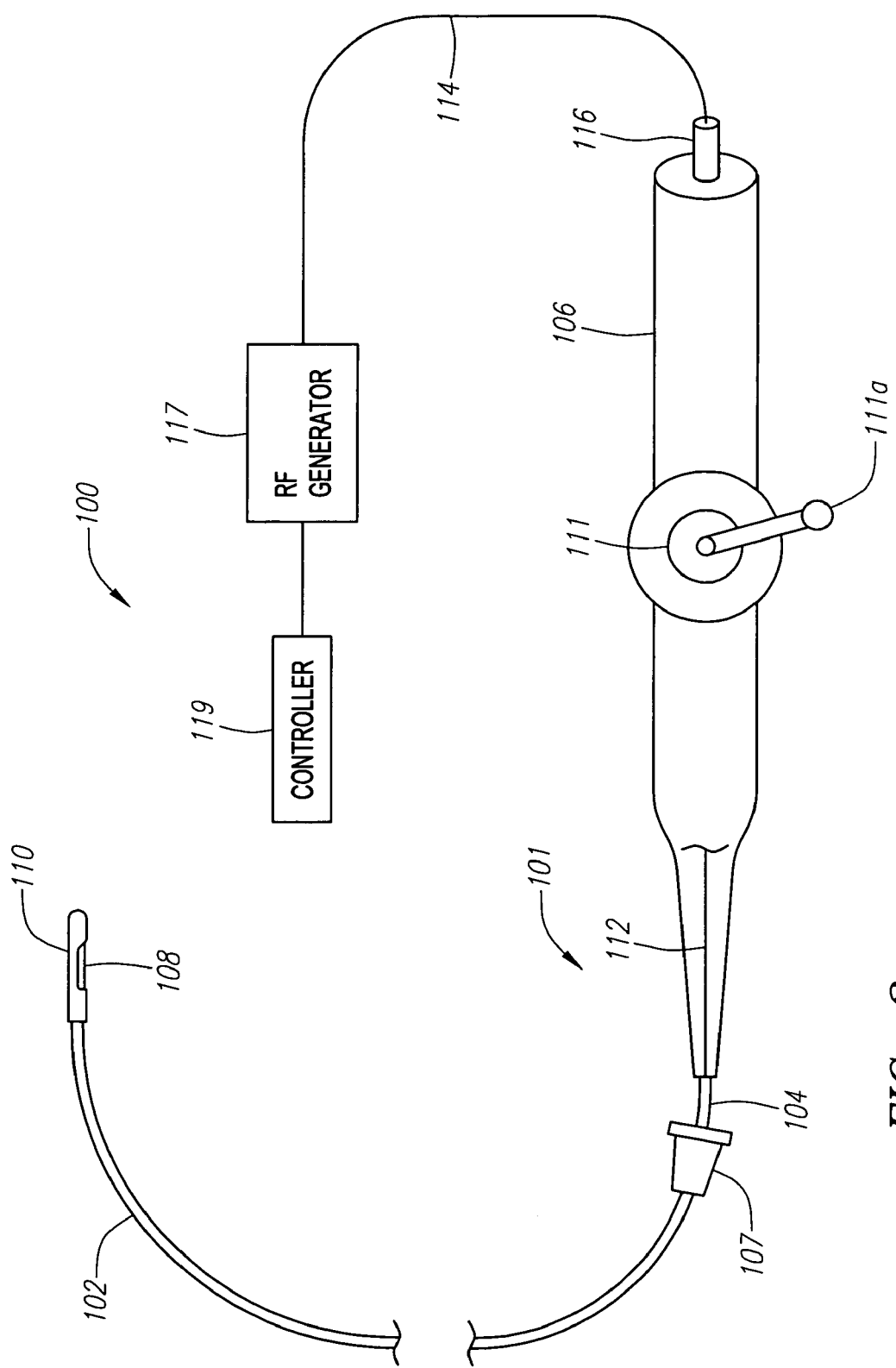
FIG. 2 shows a cardiac ablation system comprising a first, ablation catheter within a second catheter, referred to as an introducer sheath, in accordance with the invention.

FIG. 2 shows a cardiac ablation system 100 comprising a first, ablation catheter 101 within a second catheter, referred to as an introducer sheath 102, in accordance with an embodiment of the invention. The catheter 101 comprises an elongate catheter shaft 104 connected to a handle 106. The shaft 104 is inserted into the introducer sheath 102 through a Touhy Borst adapter 107. The distal end of the catheter shaft 104 supports one or more energy transmitting elements 108. A distal portion 110 of the sheath 102 extends over and covers a portion of the energy transmitting element 108 to provide electrical and thermal insulation of the covered portion of the energy transmitting element, as discussed further, below. The catheter shaft 104 exhibits sufficient torsional stiffness to enable twisting of the catheter shaft 104 by the handle 106 to be transferred to the distal end of the catheter shaft. The handle 106 preferably includes a conventional catheter steering assembly 111. The steering assembly 111 serves to deflect the distal tip of the catheter 100, and with it, the electrode 108, in response to rotation of a lever 111a, for example. Similarly, the introducer sheath 102 exhibits sufficient torsional stiffness to enable twisting of the proximal end of the sheath to be transferred to the distal portion 110 of the sheath.

The energy transmitting element 108 may be one or more electrodes electrically coupled to one or more signal wires 112 extending through the catheter shaft 104 and the handle 106. A wire or cable 114 connected to a connector 116 in the proximal end of the handle 106 connects the wires 112 to an RF generator 117. The generator 117 provides RF ablation energy to the one or more electrodes 108 under the control of a controller 119. The controller 119 controls the application of energy to the electrode 108 (or electrodes), based on temperatures sensed by one or more sensors on the electrode 108 during the ablation procedure. Predicted temperature algorithms for controlling ablation procedures are known in the art.

The introducer sheath 102 and the catheter shaft 104 are made of an inert, flexible plastic material. The sheath 102 and the catheter shaft 104 may be polyetheretherketone, such as PEEK® or polyether block amide, such as PEBAX®, which are high temperature materials that can withstand temperatures greater than 100° C.

The one or more electrodes 108 may be made of a solid, electrically conducting material, such as platinum or gold, attached to the distal end of the catheter shaft 104. Alternatively, the electrodes 108 can be formed by coating the exterior surface of an underlying support body (not shown) with an electrically conducting material, such as platinum or gold. The coating can be applied by sputtering, ion beam deposition, or equivalent techniques. Cardiac ablation catheters are discussed in U.S. Pat. No. 6,216,027 B1 and U.S. Pat. No. 6,004,269, which are assigned to the assignee of the present invention and are incorporated by reference, herein, for example. The use of multiple electrodes is described in U.S. Pat. No. 6,241,724 B1, which is also assigned to the assignee of the present invention and is incorporated by reference, herein.

Instead of being driven by an RF generator, ablation electrodes may also be heated by electrical resistance. Other energy transmitting elements that may be used with ablation catheters in any of the embodiments of the invention include microwave antennas, laser diffusing devices and ultrasound devices, for example. Cryoablation tips may also be used for ablation. Thermal insulation of cryoablation tips from the surrounding blood and tissue, which have a much higher temperature than the tips during operation, facilitates the generation of the low temperatures required to cryoablate tissue.

Figure 3A:
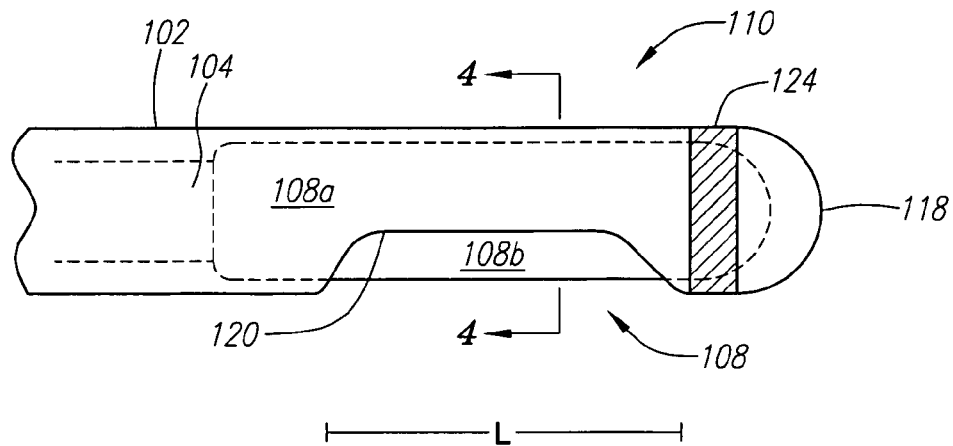
FIG. 3a is an enlarged side view of the distal portion of the introducer sheath of FIG. 2, showing a preferred configuration.
Figure 4:
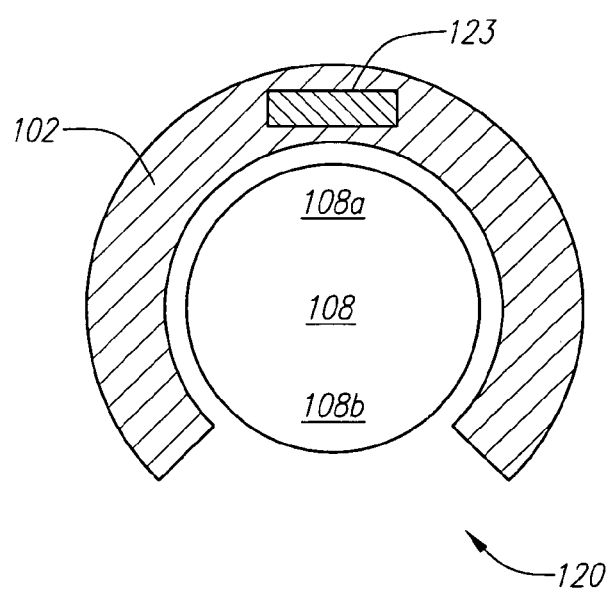
FIG. 4 is a cross-sectional view of the distal end of the introducer sheath of FIG. 3a, through line 4-4.

FIG. 3a is an enlarged side view of the distal portion 110 of the introducer sheath 102 showing a preferred configuration. Here, a single electrode 108 is attached to the distal end of the catheter shaft 104, shown in phantom. As discussed above, the distal portion 110 of the sheath 102 extends over and covers a portion 108a of the electrode 108. The covered portion 108a of the electrode 108 is also shown in phantom. The distal end 118 of the sheath 102 is closed. A radial segment 120 of the distal portion 110 of the sheath 102 is open to expose a portion 108b of the electrode 108. Preferably, the open segment 120 exposes a portion 108b of the electrode 108 having a solid angle less than about 180 degrees. About 120 degrees is more preferred, as shown in FIG. 4, which is a cross-sectional view of the distal end 110 of the introducer sheath 102 through line 4-4 in FIG. 3a. In FIG. 4, the electrode 108 is not shown in cross-section. A flatwire stiffener 123 is shown in a lumen through the shaft of the sheath 102, to provide more secure contact between the exposed portion 108b of the electrode 108 and the cardiac tissue.

The electrode is typically 3-10 mm long. The length "L" of the open segment 120 may be a few millimeters shorter than the length of the electrode 108, as shown in FIG. 3a. For example, if the electrode is 10 mm long, the length L may be 8 mm. If longer lesions are desired, the length L of the open segment may be a few millimeters longer than the electrode 108.

Radiopaque material, such as barium sulfate, is preferably mixed with the material of the introducer sheath 102, to assist in orienting the open segment 120 with respect to an ablation site under the guidance of a fluoroscope. A radiopaque marker 124 is also preferably provided at the distal end 110 of the introducer sheath 102, proximal or distal (or both) to the open portion 120. The marker can be a ring of radiopaque material, for example.

The distal end 118 of the introducer sheath 102 is preferably a rounded tip attached to the distal portion 110 of the sheath 102.

Preferably, the distal portion 110 of the sheath 102 is injection molded and bonded to a distal tip 128 of a conventional introducer sheath. The rounded tip 118 and radiopaque marker 14 could be included in the molded distal portion, as well.

Figure 3B:
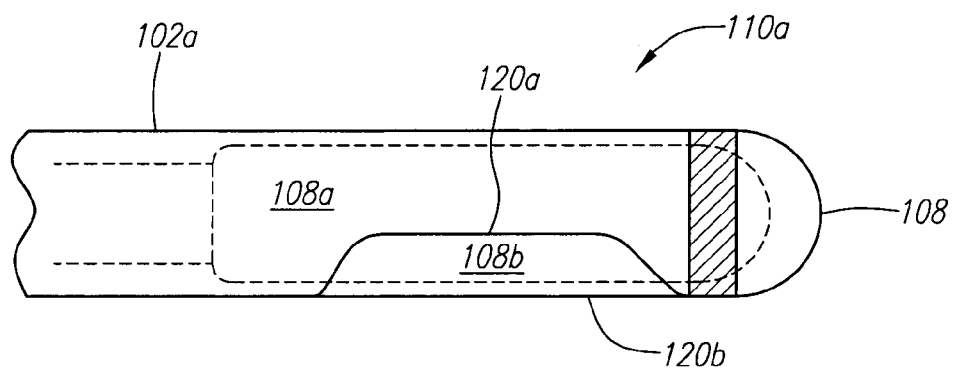
FIG. 3b is a side view of a distal portion of an introducer sheath that is similar to the distal portion of FIG. 3a, including a window of electrically conductive material.

FIG. 3b is a side view of a distal portion 110a of an introducer sheath 102a that is similar to the distal portion 110 of FIG. 3a, except that the radial open segment 120a includes a window 120b of electrically conductive material, such as an electrically conducting plastic connected to the sheath 102a, covering the open segment 120a. The exposed portion 108b of the electrode 108 is shown in phantom behind the window 120b. RF energy radiates through the window 120b, to the ablation site. The window 120b prevents blood from entering the sheath 102a. Blood entering the sheath may clot within the sheath 102, particularly between the electrode 108 and the edge of the open segment 120 in FIG. 3a. To ensure good electrical coupling between the electrode 108 and the window 120b, a flow of saline may be provided between the electrode and the window. The saline may be delivered through the introducer sheath 102. Preferably, the window 120b and the electrode 108 are separated by a small distance (about 0.003 inches-0.004 inches, 0.0762 mm-0.1016 mm for example). The electrode 108 may also be adhered to the window 120b, in which case the saline is not needed for electrical coupling.

The material of the electrically conductive window 120b should have a resistivity of less than about 1,000 ohm/cm. A window 120b of electrically conductive plastic may be formed by adding carbon black, chopped carbon fibers or metal additives to a base plastic, for example. Appropriate conductive plastics are disclosed in U.S. Pat. No. 5,846,238, which is assigned to the assignee of the present invention and incorporated by reference herein.

The window 120b of conductive plastic may be thermally bonded to the distal portion 110 of the sheath 102 by placing the distal portion and the window in a mold and applying heat. If other types of ablation energy besides RF is used, the window 120b may be made of other appropriate energy transmissive materials, such as optically transparent material for use with laser diffusing ablation devices, thermally conductive materials for use with resistive heating ablation devices and ultrasound transmissive materials for use with ultrasound ablation devices, for example.

In a catheter-based procedure in accordance with the invention, the introducer sheath 102 of FIG. 2 and FIG. 3a is inserted transcutaneously into a blood vessels, such as the femoral artery, and advanced to the site of interest. The distal portion 110 of the introducer sheath 102 is positioned, under the guidance of a fluoroscope, for example, so that the open segment 120 of the distal portion 110 faces the ablation site. The cardiac ablation catheter 101 may then be introduced into and advanced through the introducer sheath 102, to the site of interest. The ablation catheter 101 may be introduced into the sheath 102 prior to final positioning of the sheath with respect to the ablation site, as well. When the electrode 108 of the ablation catheter is advanced into the distal portion 110 of the sheath 102, the exposed portion 108b of the electrode will be adjacent to the ablation site. The distal end 110 of the sheath 102 is caused to bear against and become partially embedded in the cardiac tissue 20, so that the exposed portion 108b of the electrode 108 is at least partially embedded in the tissue, as shown in FIG. 5. Preferably, the entire exposed portion 108b of the electrode 108 is embedded in the tissue. Ablation energy is then applied to the electrode 108 through the RF generator 117. The distal portion 110 of the introducer sheath 102 shields the covered portion 108a of the electrode 108, much of which would not be in contact with the cardiac tissue at the ablation site, from the blood "B" circulating through the heart chamber 18. The RF energy is therefore substantially blocked from being emitted through the covered portion 108a of the electrode 108 to the circulating blood. As a result, the dissipation of energy into the blood pool is decreased and more of the ablation energy provided to the electrode 108 is emitted from the exposed portion 108b directly to the ablation site. Total power requirements of the ablation treatment are thereby reduced.

In addition to providing electrical insulation, the distal portion 110 of the introducer sheath 102 thermally insulates the electrode 108 and the tissue of the ablation site from the blood circulating through the heart or blood vessel. During a typical RF ablation procedure, the tissue at the ablation site is heated due to the application of RF energy by the electrode 108. The heated tissue heats the electrode 108, where the temperature sensor or sensors are typically located (See FIG. 1). The output from the temperature sensor is used to control the continued application of energy in the procedure, under software control. During the procedure, however, the cooler blood B dissipates heat from the tissue. The hottest tissue is therefore typically about 1-2 mm below the surface of the tissue contacting the electrode. The electrode 108 may only be heated to the temperature at the surface of the tissue, which may be up to about 30 degrees lower than the temperature of the hottest tissue. In addition, heat is dissipated from the electrode 108 itself to the cooler blood. The temperature sensed by the sensor or sensors on the electrode may therefore be less than the hottest temperature of the tissue. The temperature difference may interfere with the control of the ablation procedure. Coagulum and popping may result.

The temperature sensed by a sensor or sensors on the electrode 108 shielded in accordance with the invention, in contrast, more closely matches the actual tissue temperature at the ablation site. The regulation of the RF or other such energy is therefore more accurate. Coagulum and popping are thereby reduced. Embodiments that provide further insulation of the tissue at the ablation site as well the electrode are discussed below.

The introducer sheaths of the invention may include specialized curves and the lengths of the open segments may be varied to target different ablation sites. Specially-shaped segments in different locations in the distal portions of the sheaths could accommodate different expected angles of attack between the tip and tissue, from about 0° (substantially parallel to the tissue at the ablation site, as shown in FIG. 5) up to almost 90° at different tissue locations. The embodiment of FIGS. 2-4, with a radial segment 120, is preferred where the expected angle of attack that is substantially parallel to the tissue.

FIG. 6 is a side view of another embodiment of an introducer sheath 150 having a distal portion 152 with an open section 154, which is preferred for use where the expected angle of attack is from about 10° to about 45°. Here, the open section 154 includes a portion 156 of the distal end 158 of the sheath 152, as well as a radial portion 160. The open section 154 exposes a portion 108b of the electrode 108, providing electrical and thermal insulation of the covered portion 108a. A radiopaque marker 162 is preferably provided at the distal end of the distal portion 152 to enable identification of the distal end on a fluoroscope. The electrode 108 on the ablation catheter 101 of FIG. 2, for example, may be readily aligned with the open section 154 of the distal portion 152 so that a portion 108b of the electrode 108 is exposed and a portion 108a (shown in phantom) is insulated, under the guidance of a fluoroscope. Alternatively, indicia may be provided on the proximal end of the catheter shaft 101 to indicate the distance of the distal end of the electrode 108 from the distal end 158 of the sheath 150, for example. The indicia may comprise colored markings, for example.

FIG. 7 is a side view of the distal portion 152 of FIG. 6, with a front half of the distal portion 152 of the sheath 150 removed. The entire electrode 108 and the catheter shaft 101 are shown in relation to the rear portion of the distal sheath portion 152.

Other angles of attack may be accommodated by varying the distance from the distal end of the electrode to the distal end 158 of the sheath 152. The axial length of the open segment 154 may also be varied.

Figure 8:
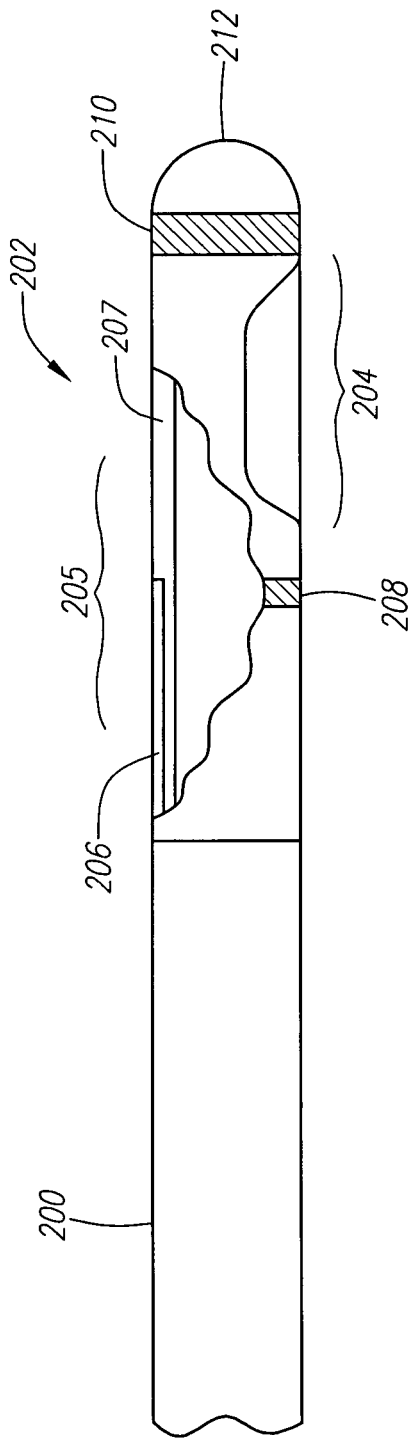
FIGS. 8 and 9 are side views of an introducer sheath as in FIG. 3a, including a bendable section.
Figure 9:
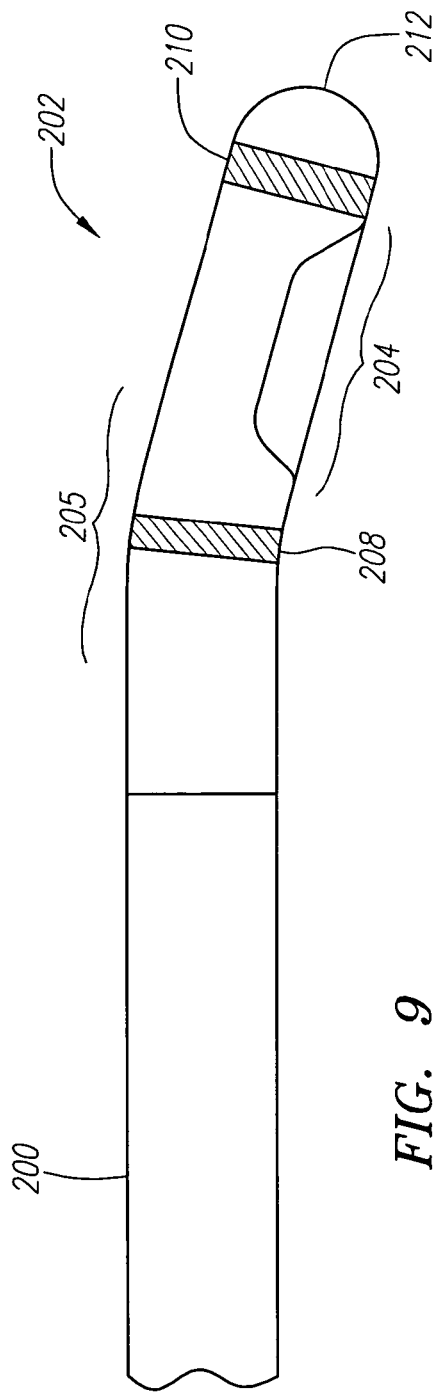

FIGS. 8 and 9 are side views of another introducer sheath 200 wherein the distal portion 202 includes a radial open segment 204, as in the embodiment of FIG. 3a, and a bendable section 205. The catheter shaft 101 and electrode 108 are not shown within the sheath 200 in FIGS. 8 and 9. The ability to bend the sheath 200 assists in navigating the introducer sheath 200 through curves in blood vessels and the heart as the sheath 200 is advanced to the ablation site. It also assists in pressing the electrode of the ablation catheter more firmly into the tissue at the ablation site. In FIG. 8, the portion of the sheath 200 over the bendable section 205 is partially cutaway. A pre-bent stylet wire 206 is provided in a lumen 207 in the sheath 200, to control the bending and straightening of the sheath 200. The bendable section 205 of the sheath 200 is composed of a softer durometer material than the remainder of the sheath, facilitating bending. A radiopaque marker 208 is preferably provided around the bendable section 205 for identification on a fluoroscope. In FIG. 8, the bendable section 205 is straight. When the stylet wire 206 is pushed forward and the bend in the wire coincides with the bendable section 205, the sheath 200 bends. The stylet wire 206 can be remotely controlled through a handle (not shown) coupled to the proximal end of the introducer sheath 200. Another radiopaque marker 210 and a soft tip 212 are preferably provided as well, as discussed above.

Figure 10:
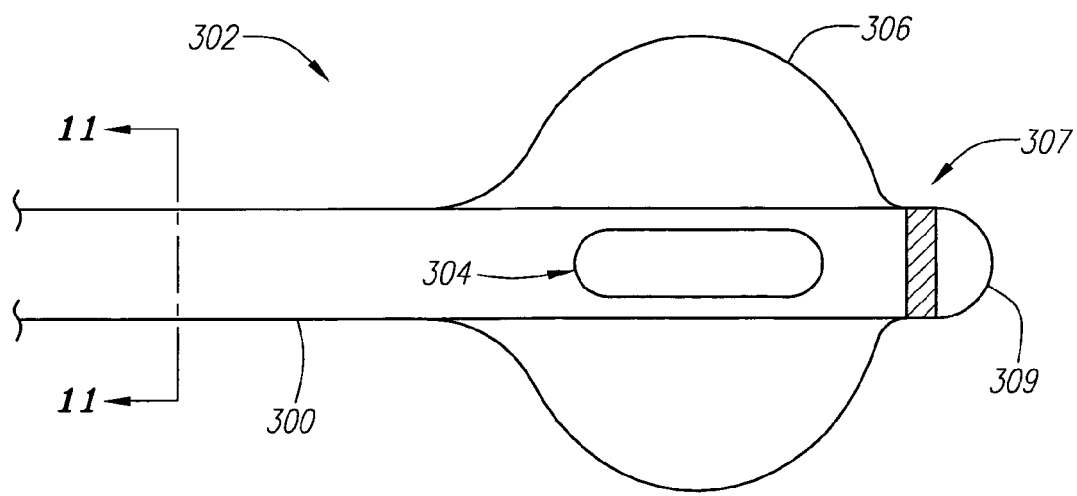
FIG. 10 is a bottom view of another introducer sheath in accordance with the invention, having a distal portion with a radial open segment and an inflated balloon behind the open segment.

As mentioned above, additional structures may be provided on the introducer sheath for further thermal and electrical insulation of the electrode and the tissue at the ablation site. FIG. 10 is a bottom view of another introducer sheath 300 having a distal portion 302 with a radial open segment 304 to expose a portion of an electrode carried by an ablation catheter (not shown). An inflatable insulation balloon 306 is bonded to the distal portion 302, around a part of the circumference of the distal portion 304 behind the radial open segment 304. The balloon 306 is connected to the distal portion of the sheath 302, to cover about the rear half of the sheath, behind the open segment 304 (best shown in FIG. 12, discussed below). A radiopaque marker 307 and a soft tip 309 are preferably provided, as well. The introducer sheath 300 can also include a bendable section as in FIG. 8.

Figure 11:
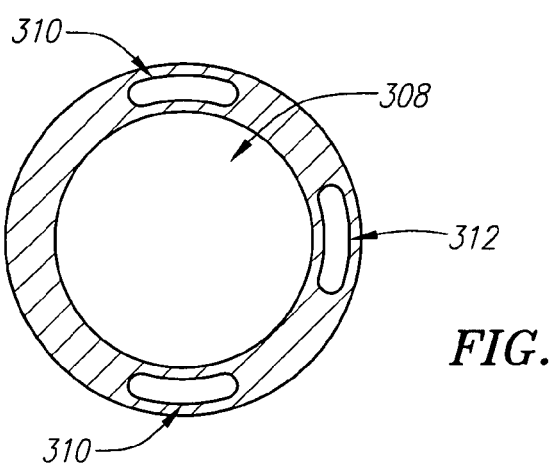
FIG. 11 is a cross-sectional view of the introducer sheath of FIG. 10, through line 11-11.

FIG. 11 is a cross-section through line 11-11 of the catheter of FIG. 10, showing a lumen 308 for receiving the ablation catheter and lumens 310 for conveying fluid for inflating and deflating the balloon 306. A lumen 312 is also shown receiving a flatwire stiffener, as discussed above.

The insulation balloon 306 is preferably a material with a melt temperature greater than about 100° Centigrade and a softening temperature greater than about 80° Centigrade. Silicone rubber, latex, polyurethane, polyether block amide, such as PEBAX®, or polyetheretherketone, such as PEEK®, may be used, for example.

Figure 12:
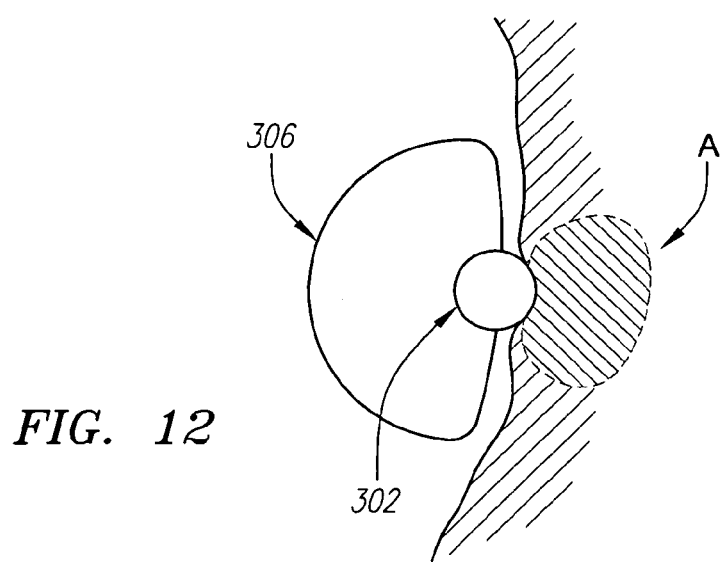
FIG. 12 is a front view of the distal portion of the introducer sheath of FIG. 10 adjacent to tissue at an ablation site.

FIG. 12 is a front view of the distal portion 302 of the introducer sheath 300 with the balloon 306 inflated, adjacent to tissue at an ablation site "A". When inflated, the surface of the balloon 306 is preferably in contact with the tissue or is close enough to the tissue to create a substantially static blood pool adjacent to the electrode, to substantially prevent convective transport of heat away from the ablation site, decreasing the dissipation of heat from the tissue to the blood. The circulating blood is also distanced from the electrode (not shown) within the distal portion 302 of the sheath, further decreasing heat dissipation from the electrode. The electrode temperature therefore more closely matches the temperature of the tissue at the ablation site, enabling more accurate temperature regulation of the ablation process. Since the heat dissipation from the tissue at the ablation site is decreased, the power required to achieve effective ablation temperatures of the tissue is also therefore decreased.

In addition, when the ablation site is within an orifice, such as a pulmonary vein, the rear surface of the balloon 302 can press against the orifice wall, pushing the opposing side of the distal portion 302 of the introducer sheath 300 and the electrode within the distal portion, against the tissue at the ablation site. The contact between the electrode and the tissue is thereby improved. To create a circumferential lesion in the orifice, the entire sheath may be rotated while the electrode is within the distal portion. The open segment 304 would thereby expose different circumferential portions of the electrode to different circumferential portions of the orifice, creating a circumferential lesion. While discussed with respect to an introducer sheath as in FIG. 3a, an inflatable balloon can be readily used with an introducer sheath as in FIG. 6, as well.

Figure 13:
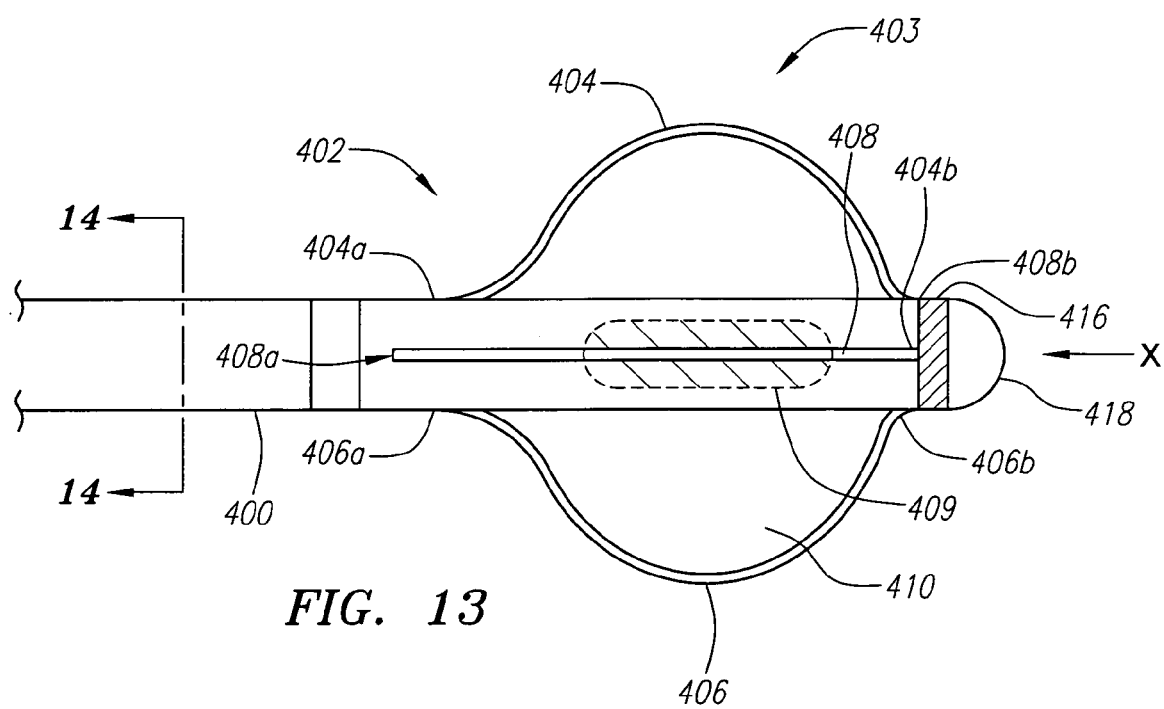
FIG. 13 is a top view of another introducer sheath in accordance with the invention, with an expandable insulation web attached to the distal portion.
Figure 14:
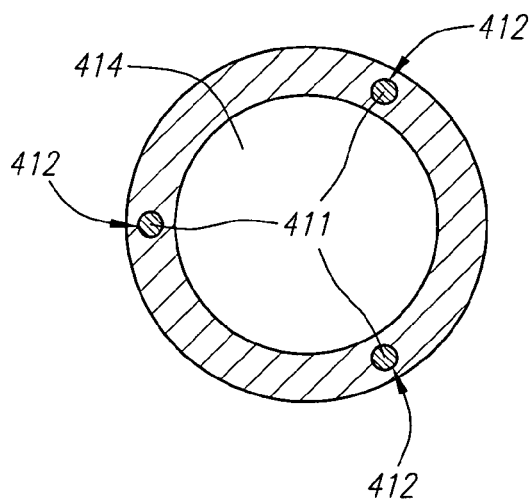
FIG. 14 is a cross-sectional view of the introducer sheath of FIG. 13, through line 14-14.

Instead of a balloon, an expandable web may be provided for further thermal and electrical insulation, as shown in FIGS. 13-17. FIG. 13 a top view of an introducer sheath 400 with a distal portion 402 having an expandable insulation web 403 attached thereto. A radial open segment 409, which is located at the bottom of the sheath 400 in this view, is shown in phantom. The web 403 is composed of splines 404, 406, and 408 surrounded by an elastic, insulative material 410. In this example, distal ends 404a, 406a, 408a of each of the splines are connected to the sheath 400 distal to the location of the electrode (not shown) when the ablation catheter is within the introducer sheath 400. Proximal ends 404b, 406b, 408b of each of the splines are connected to respective stylet wires 411 that extend through lumens 412 in the sheath 400, as shown in FIG. 14. FIG. 14 is a cross-sectional view of the introducer sheath 400 of FIG. 13, through line 14-14. The stylet wires 411 may be remotely controlled through a handle (not shown) coupled to the proximal end of the introducer sheath 400. A lumen 414 for receiving the ablation catheter is also shown. A radiopaque marker 416 and a soft tip 418 are preferably provided as well, as discussed above.

The splines 404, 406, 408 are pre-bent. When one or more of the stylet wires 411 are pulled back, the respective spline is straightened so that it lies adjacent to the sheath 400. When one or more of the stylet wires 411 are pushed forward, the respective spline returns to its pre-bent position pushing out the adjacent portion of the elastic material 410, creating the web 403. The web 403 is an elastic material with a melt temperature that is preferably above about 80° Centigrade. Latex, silicone rubber, polyether block amide, such as PEBAX®, and low durometer polyurethane may be used, for example. The splines 404, 406, 408 may be made of nitinol, for example.

Figure 15:
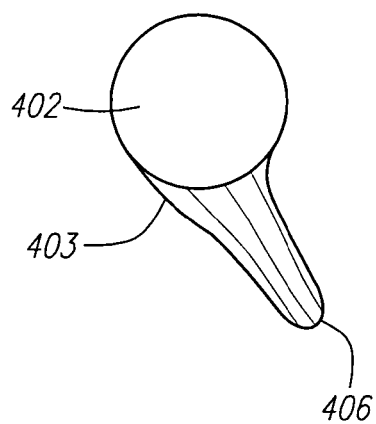
FIG. 15 is a front view of the distal portion of the introducer sheath of FIG. 13 along arrow X in FIG. 13.
Figure 16:
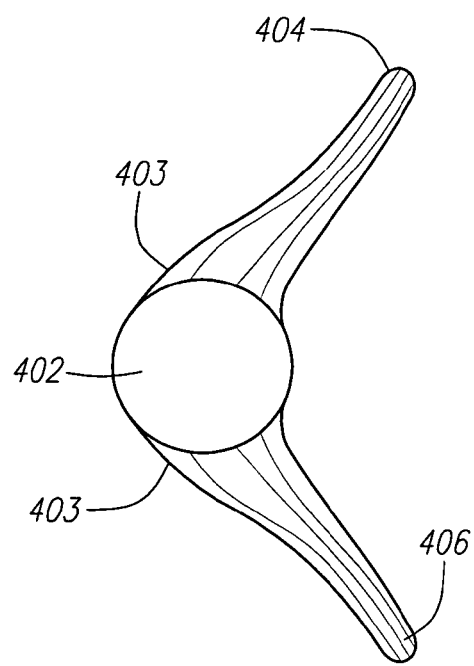
FIG. 16 is a front view of the introducer sheath of FIG. 13, with two splines of the web extended.
Figure 17:
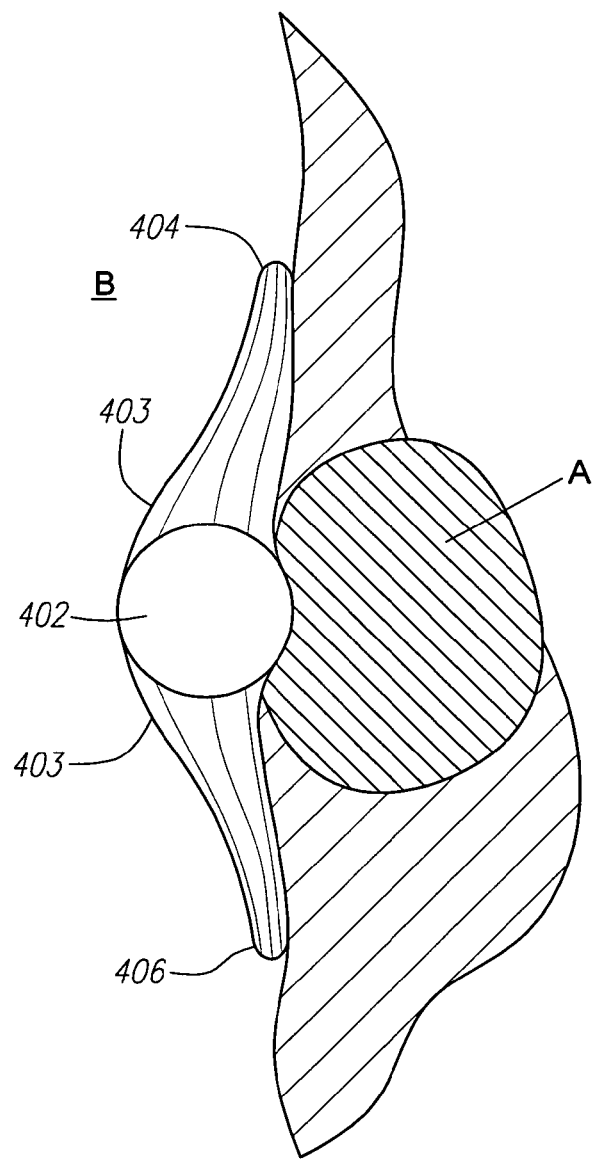
FIG. 17 is a front view of the distal end of the introducer sheath of FIG. 16 pressed against the body tissue at an ablation site.

FIG. 15 is a front view of the distal portion 402 of the catheter 400 of FIG. 13 along arrow "X," with one spline 406 partially extended. FIG. 16 is a front view of the same catheter 400, with two splines 404, 406 extended. FIG. 17 is a front view of the distal end 402 of the catheter 400 with two splines 404, 406 extended and pressed against the body tissue at an ablation site A. The web 403 is adjacent to or contacts tissue proximate the ablation site A, insulating the tissue from heat dissipating to the blood.

As above, if the ablation site is within an orifice, expansion of the spline 408 would expand the web 403 so that it would press the energy transmitting member against the tissue at the ablation site A.

In the embodiments and configurations described above, the introducer sheaths of the present invention may be used with any commercially available ablation catheter with one or more energy transmitting elements at its distal end, that will fit within the sheath. Deeper lesions may be created at currently available power levels, since less of the ablation energy is lost to the blood. Lesions in which the depth has been "power limited" in the past may become more consistently achievable. Larger electrodes could also be used at the same power levels as smaller electrodes are used today, eliminating concerns over the use of higher powers.

Instead of providing a balloon or web on the introducer sheath, as described above, a balloon or web may be provided on the ablation catheter or probe itself, to surround and insulate a portion of the electrode, as well as tissue at the ablation site.

Figure 18:
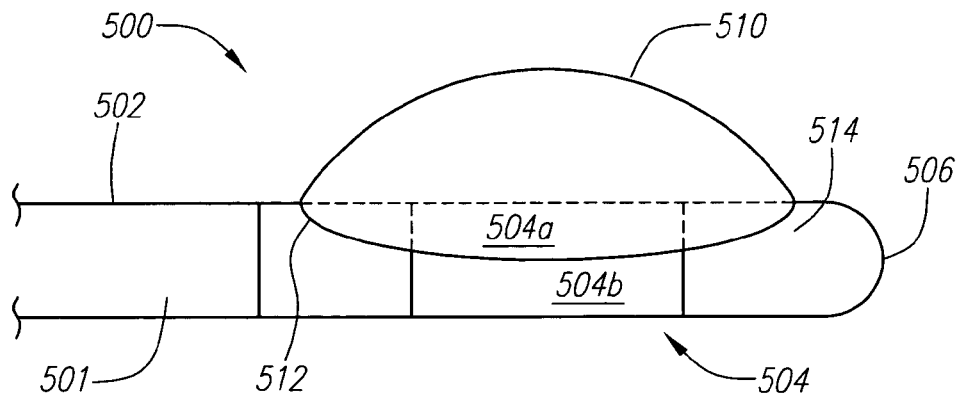
FIG. 18 shows a distal portion of an ablation catheter in accordance with another embodiment of the invention, including an inflatable balloon insulating a portion of an electrode.

FIG. 18 shows a catheter 500 including a catheter shaft 501 with a distal portion 502. An energy transmitting element, such as an electrode 504, is supported by the distal portion 502. The electrode 504 is spaced from the distal end 506 of the catheter 500. A balloon 510 has proximal and distal ends 512, 514, respectively, attached to the catheter shaft 500 proximal and distal to the electrode 504, respectively. The balloon 510 is preferably positioned to cover up to half of the circumferential surface of the electrode 504, to provide electrical and thermal insulation of the covered portion 504a of the electrode 504. The balloon 510 may be attached to the electrode 504, as well, but that is not required. The covered portion 504a is shown in phantom in FIG. 18. The exposed portion 504b may be brought into contact with tissue for ablation. One or more lumens are provided in the catheter shaft 501 to convey fluid to and from the balloon 510 to inflate and deflate the balloon, respectively. A flatwire stiffener (not shown) may be provided in a lumen in the catheter sheath 501, as well.

Figure 1:
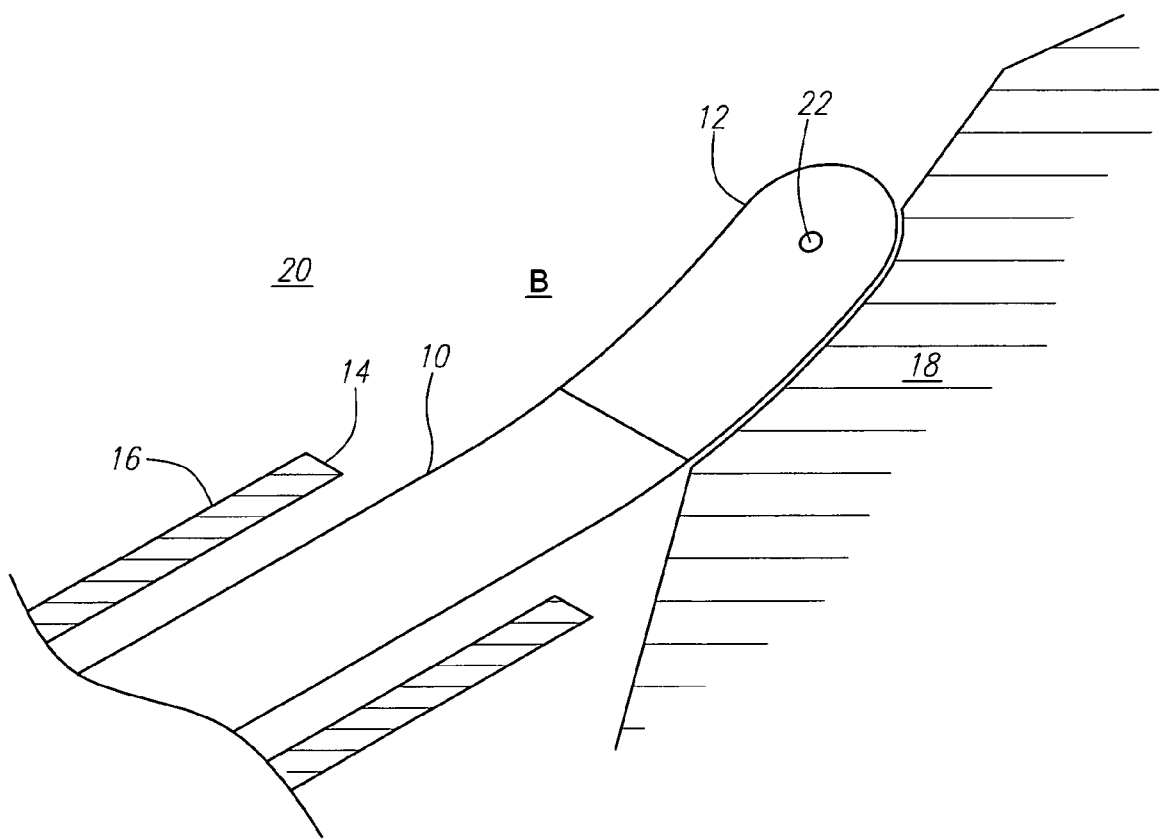
FIG. 1 is a view of a distal end of a typical ablation catheter including one or more energy transmitting elements extending through a distal end of an introducer sheath at an ablation site in a chamber of the heart.

To use the ablation catheter 500, the catheter is advanced to a site of interest through a conventional introducer sheath 16, as in FIG. 1. The distal portion 501 of the catheter 500 is advanced completely out of the distal end of the sheath 16, so that the electrode 504 and the balloon 510 are not within the sheath. The electrode 504 is positioned adjacent to the tissue at the ablation site under the guidance of a fluoroscope and the balloon is inflated. Pressure is applied against the electrode toward the tissue with the assistance of a flatwire stiffener, for example, or the balloon 510 (if the ablation site is within an orifice as discussed above) and ablation energy is provided to the electrode 504 to ablate tissue at the site. When the procedure is completed, the balloon 510 is deflated and the distal portion 501 of the catheter 500 is withdrawn into the introducer sheath 16. The entire catheter 500 is then withdrawn from the introducer sheath 16.

Figure 19:
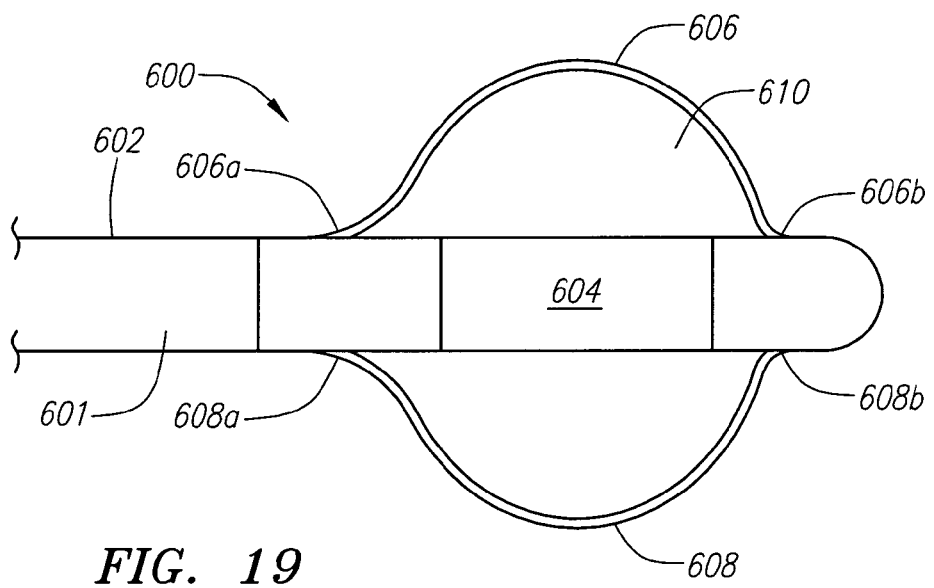
FIG. 19 is a bottom view of an ablation catheter in accordance with another embodiment, comprising a catheter shaft with a distal portion including a web of elastic material partially insulating an electrode.

FIG. 19 is a bottom view of a catheter 600 in accordance with another embodiment, comprising a catheter shaft 601 with a distal portion 602 including an electrode 604. Splines 606, 608 are shown in this view, supporting a web 610 of elastic material. Proximal ends 606a, 608a of the splines are connected to the catheter shaft 601 proximal to the electrode 604. Distal ends 606b, 608b are connected to the catheter shaft distal to the electrode 604. One or more additional splines may be provided between the splines 606, 608, as well. The splines 606, 608 (and others if provided) are pre-bent to expand the web 610. When the cardiac ablation catheter 600 is advanced through an introducer sheath, such as the introducer sheath 16, the sheath compresses the splines 606, 608 and the web 610. When the distal portion 602 of the catheter 600 is advanced out of the distal end of the sheath 16, the splines 606, 608 return to their pre-bent condition, opening the web 610. When the distal end 602 of the catheter 600 is withdrawn back into the introducer sheath 16 to be removed from the body, the sheath 16 again compresses the splines.

In another configuration, the proximal ends 606a, 608a of the splines 606, 608 may be connected to respective stylet wires (not shown) extending through respective lumens in the catheter shaft 601. As described above with respect to the embodiment of FIGS. 13-17, wi0thdrawing one or more of the stylet wires flattens the respective spline and advancing of one or more of the stylet wires returns the respective stylet to their pre-bent position, opening the web.

Figure 20:
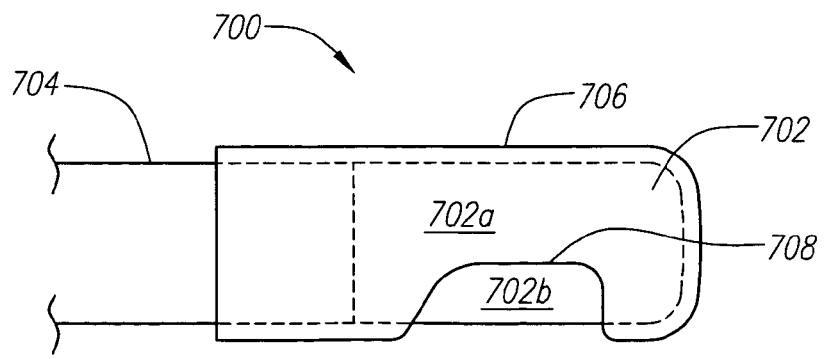
FIG. 20 is side view of an ablation catheter in accordance with another embodiment the invention, wherein a cover of insulating material partially insulates the electrode.

FIG. 20 is side view of a distal portion of another embodiment of an ablation catheter 700, comprising an electrode 702 connected to a distal end of a catheter shaft 704. A cover 706 of insulating material is bonded or otherwise attached to the distal portion of the catheter shaft 704 proximal to the electrode 702 and over a portion 702a of the electrode. An open segment 708 is provided in the cover 706 to expose a portion 702b of the electrode 702. The open segment 708 has the characteristics of the open segment in the introducer sheaths discussed above. For example, the open segment 708 preferably extends over a circumferential angle of less than 180°. About 120° is preferred. The shape and location of the open segment 708 may be adapted for an angle of attack of greater than about 10 degrees, as shown above with respect to the embodiment of FIGS. 6-7. An inflatable balloon or an expandable web, discussed 00above, can also be provided over the cover 706, behind the open segment.

While the invention has been described with respect to the use of catheters in cardiac ablation treatment, the invention may be used on catheters for other ablation procedures in other parts of the body as well, such as in the remainder of the circulatory system, other soft tissue, such as the liver, the kidneys, and the brain, the pancreas, the lungs, the prostate and in the soft tissue of the bones, for example.

The invention may also be used in many laparoscopic probe-based procedures. Laparoscopic probes provide minimally invasive direct access for introducing ablation elements into interior body regions through body cavity walls. In the specification and claims, the term "catheter" is meant to encompass hand held probes of any type, as well. Other energy transmitting devices may benefit from the present invention, as well.

One of skill in the art will understand that modifications may be introduced into the embodiments described above without departing from the scope of the invention, which is defined in the claims, below.

We claim:

1. An ablation probe, comprising:
   an elongated shaft having a distal portion;
   a tissue ablative element carried by the distal shaft portion;
   a sheath having a distal portion composed of an electrically insulative material for covering the tissue ablative element, the sheath further having a window composed of an energy transmissive material through which ablation energy from the ablative element may pass into adjacent body tissue, the energy transmissive material being different from the electrically insulative material, the window and ablative element being separated; and
   a lumen configured for conveying an electrically conductive fluid between the ablative element and the window.

2. The ablation probe of claim 1, wherein the elongated shaft is flexible.

3. The ablation probe of claim 1, wherein the ablation energy is radio frequency (RF) energy, and the energy transmissive material is an electrically conductive material.

4. The ablation probe of claim 3, wherein the window is disposed on the distal portion of the sheath.

5. The ablation probe of claim 1, wherein the window is composed of an electrically conductive plastic.

6. The ablation probe of claim 1, wherein the window is configured to allow passage of the ablation energy over an angular range radial to the shaft.

7. The ablation probe of claim 1, wherein the distal portion of the sheath has an open segment, and the window is disposed over the open segment.

8. An ablation system, comprising:
   the ablation probe of claim 1; and
   a source of ablation energy coupled to the ablative element.

9. A method of ablating tissue using the ablation probe of claim 1, comprising:
   placing the distal shaft portion adjacent the body tissue; and
   conveying ablation energy from the ablative element, through the window, and into the body tissue.

10. An ablation probe, comprising:
    an elongated shaft having a distal portion;
    a tissue ablative element carried by the distal shaft portion;
    an insulative sheath covering the tissue ablative element, the sheath having a window composed of an electrically conductive material through which ablation energy from the ablative element may pass into adjacent body tissue, the window and ablative element being separated;
    a lumen configured for conveying an electrically conductive fluid between the ablative element and window.

11. The ablation probe of claim 10, wherein the elongated shaft is flexible.

12. The ablation probe of claim 10, wherein the ablation energy is radio frequency (RF) energy.

13. The ablation probe of claim 10, wherein the electrically conductive material is electrically conductive plastic.

14. An ablation system, comprising:
    the ablation probe of claim 10; and
    a source of ablation energy coupled to the ablative element.

15. A method of ablating tissue using the ablation probe of claim 10, comprising:
    placing the distal shaft portion adjacent the body tissue; and
    conveying ablation energy from the ablative element, through the window, and into the body tissue.

* * * * *